United States Patent
Linseth

[11] Patent Number: 6,012,415
[45] Date of Patent: Jan. 11, 2000

[54] BOLUS WITH ANIMAL ID AND TEMPERATURE TRANSPONDER

[75] Inventor: Gerry S. Linseth, Rapid City, S. Dak.

[73] Assignee: Magtronic ID, Inc., Cody, Wyo.

[21] Appl. No.: 08/843,541

[22] Filed: Apr. 18, 1997

[51] Int. Cl.⁷ .............................. A01K 29/00; A61B 5/00
[52] U.S. Cl. ........................................... 119/174; 128/899
[58] Field of Search ................... 119/51.02, 174; 128/899; 607/156

[56] References Cited

U.S. PATENT DOCUMENTS

| | | | |
|---|---|---|---|
| 4,854,328 | 8/1989 | Pollack | 119/51.02 X |
| 5,322,034 | 6/1994 | Willham et al. | 119/51.02 X |
| 5,697,384 | 12/1997 | Miyawaki et al. | 128/899 |

*Primary Examiner*—Robert P. Swiatek
*Attorney, Agent, or Firm*—Dorsey & Whitney LLP

[57] ABSTRACT

A method and apparatus for remotely reading programmed and programmable memories implanted in livestock and particularly, ruminants, for maintaining animal identification, temperature, medial history, etc. A bolus in commonly implanted in the rumen or first stomach of such an animal to prevent "Tarmumatic Retuculoperitonitis" commonly known as hardware disease in cattle. This disclosure is directed to utilizing a bolus formed from a rectilinear ferrite block magnet of sufficient dimensions and weight for its purpose and attaching a transponder chip to the outer surface of the bolus and including on that chip a plurality of memories capable of having the animal identification on one memory, a temperature sensing device, a programmable memory for programming medical information during the life of the animal and additional memories or specific sensing device which can be read or programmed external of the animal by means of a reader/programmer which can activate and power the transponder chip to make selected memory readings or programming. An antenna for the transponder operation is wrapped around the bolus magnet and attached thereto. A protective sleeve may be utilized to ease implant of the device.

10 Claims, 2 Drawing Sheets

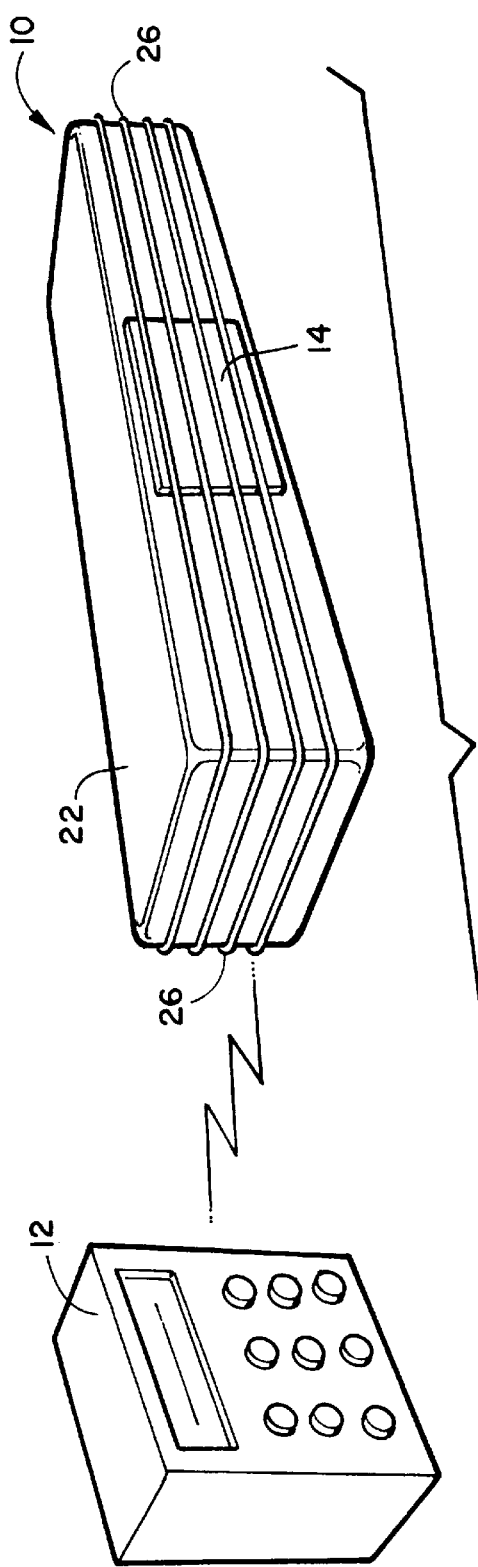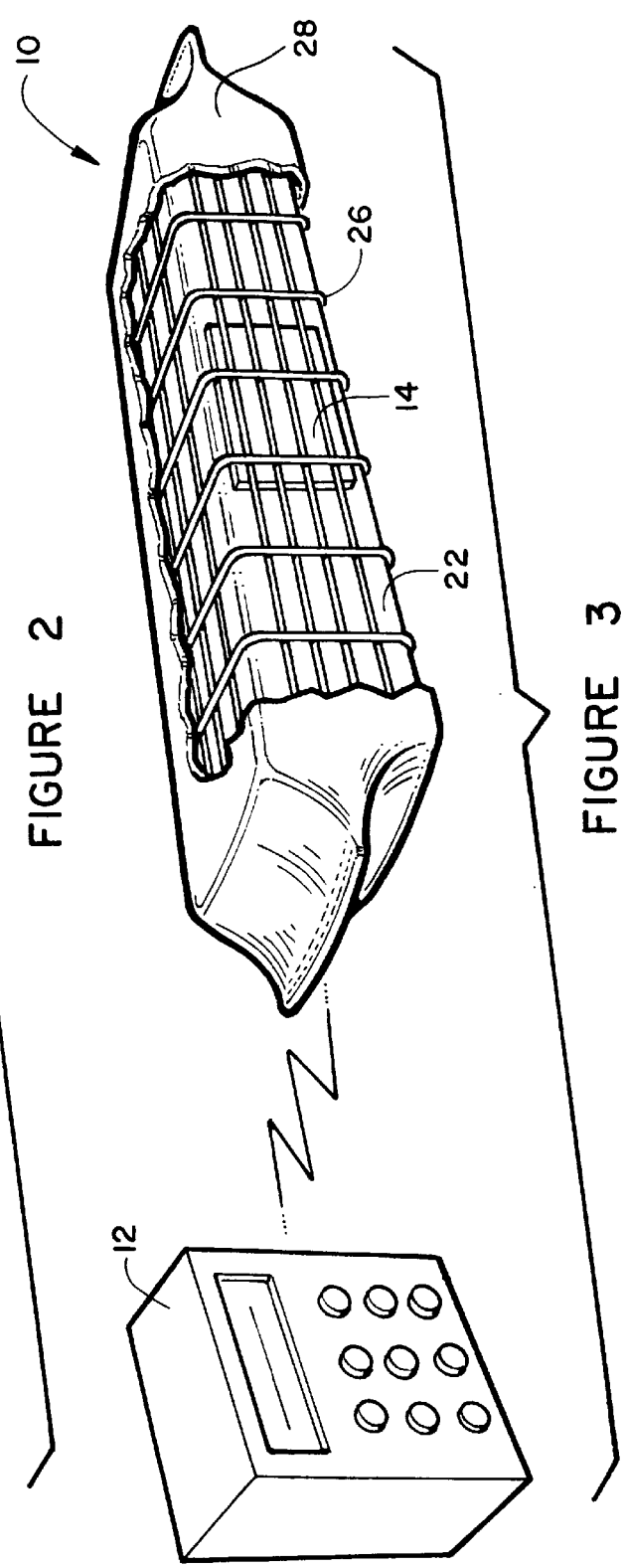

BOLUS WITH ANIMAL ID AND TEMPERATURE TRANSPONDER

BACKGROUND OF THE INVENTION

The present invention relates to a system for animal identification and more particularly to a system for electronically tagging and monitoring the body temperature of livestock using internal transponders that are integral with a bolus and made to reside in the reticulum or rumen of ruminants.

It is well known to have ruminant animals ingest a permanent magnet so that any ferrous material that is ingested by the animal will be retained by the magnet in the reticulum rather than any ferrous material passing through the animal causing possible internal injury to the animal.

U.S. Pat. No. 4,262,632 to inventors Hannon et al. teaches an electronic identification system for ruminant animals comprising a transmitter capsule precoded to broadcast a series of binary pulses peculiar to the animal, the transmitter capsule being designed by adjusting its specific gravity to reside permanently in the animal's second stomach or reticulum. The electronics are encapsulated in a housing of a material which can be accepted physiologically by the animal and yet not be attacked by other contents in the animals reticulum. The specification indicates that capsules with specific gravity of approximately 1.7 or greater have successfully retained and permanent retention is assured with specific gravity of 2 or greater. In the preferred embodiment, the electronics and a weight are inserted in a glass housing and the capsule is then evacuated and sealed off. Quartz and fiberglass are also mentioned as suitable materials for the housing.

U.S. Pat. No. 5,482,008 by inventors Stafford et al. teaches a bolus for administration to a ruminant animal and for retention in the rumen or reticulum of the animal, the bolus having an electronic identification device housed therein with an identification code encoded in the electronic device, and a permanent visual representation of the identification code on and/or within the bolus.

Traumatic Retuculoperitonitis, known more commonly as hardware disease in cattle, is an infection in the stomach wall caused by swallowing of dangerous metal objects which penetrate and embed themselves in the stomach wall. The disease can be fatal once hardware starts to affect the heart and liver organs. Serval types of dangerous metal objects when swallowed can cause hardware disease in cattle. Wire that is used in hay bales or pieces of barbwire that is left scattered on the ground are two worst types of metal for cattle. To prevent hardware disease, bolus permanent magnets are routinely placed in the reticulum of ruminant animals which collect these dangerous metal objects and prevent their penetration into vital origins of the an animal.

The device of Stafford et al. is not practical as in addition to the teaching of Stafford et al. an additional magnetic bolus must also be ingested by the same animal to preform its purpose. In addition the Stafford et al. device is fragile in construction see column 7, at lines 52–67 of the patent and with normal animal activity the device of Stafford et al. could bang against a magnetic bolus causing damage, inoperable or inaccuracy to the Stafford et al device. As the magnetic bolus in the same animal acquired ferrous material the Stafford device would become even more susceptible to damage or destruction. Also it is believed that a magnetic field adjacent to the Stafford et al. device would interfere with its expected operation if a specific magnetic flux orientation relative to the Stafford et al. described transponder was not maintained.

There is a need for a combination magnetic identification and temperature bolus. A bolus of this type would find wide spread acceptance in the field of ruminating animal husbandry.

SUMMARY OF THE INVENTION

The instant invention is directed to an improved bolus having expanded features over the current state of the art. The bolus combines a rectilinear shaped coated ferrite block magnet of sufficient dimensions to serve the purpose intended. Generally stated that purpose is a magnet of sufficient weight to maintain a position in the rumen or reticulum of an animal for the term of its life and then reusable for an indefinite number of future animals and to contain small micro chip technology to enable identification of a given animal, monitor that animal's temperature, maintain any medical information for that animal which can be upgraded throughout the animal's life and other future requirements dictated by the government or other regulatory departments.

Along these lines, Applicant has designed and perfected such a combination bolus.

Applicant device comprises a rectangular coated ferrite block magnet onto which is attached a transponder chip with a plurality of read or write memories excitable from an external reader and preprograming with an identification number assigned to a particular animal, a readable memory which monitors the temperature of the animal in which it is contained, a writable memory that can be programed on occasion during the life of the animal to maintain complete medical records of that animal which cannot be erased during the life of the animal. The transponder being capable of being excited by various operating frequencies transmitted by a reader/programmer located externally of the animal by a state of the art reader/programmable device. Depending on the excitation frequency one of the memories can be caused to transmit information therefrom which registers on the reader/programmer.

The transponder is attached to one of the flat surfaces of the magnet

As each bolus of the invention is implanted in an animal the ID number with the owner's name, address, phone number and implant date will be sent in for entry in the national or international data bank. When the animal is sold the name, address, phone number and date of sale will be sent to the data bank to upgrade the information on the animal and assign the ID number to the new owner. Each additional time that animal has been transferred the data bank will be provided updated information on the new owner.

An antenna is interconnected to the transponder for receiving a signal from and transmitting a signal to comprises a plurality of wire wraps around the bolus. It has been found that good results are obtained when the wire is wrapped substantially on a plane normal to the field direction of the permanent magnet or in a direction in an orientation which causes induced magnetic field from the permanent magnetic. It has been found that even a randomly wrapped antenna is suitable to operate the system. The complete unit can then be potted with an epoxy or any other coating suitable for the purpose intended that is to maintain the components on the bolus magnet and not adversely effect the animal in which it is planted. In additional the entire unit can be covered with a shrink sleeving with the ends sealed to improve the life of the bolus and to make it smoother and easier to place in the animal.

It is an object of this invention to provide a single bolus to provide a plurality of different information from a live animal of the type described in which bolus is inserted while additionally providing a conventional permanent magnet for the attraction of ferrous materials ingested by that animal.

It is a further object of this invention to provide a bolus on which the identification of the animal is contained that cannot be altered externally of that animal.

Another object of this invention is to provide the temperature of that animal on demand from a reader external of that animal and spaced therefrom.

Still another object of this invention is to provide a transponder whereby information can be read and/or programed into that memories carried by the transponder but cannot be altered externally of and animal into which it is placed.

Yet still another object of this invention is to provide a central register where ownership information for any animal having this bolus of this invention placed at any time during its life.

Other objects, advantages and applications of the invention will become apparent to those skilled in the art upon consideration of the following more detailed description taken along with the following drawing Figures:

BRIEF DESCRIPTION OF THE DRAWING FIGURES

FIG. 2 is a showing of an embodiment of the invention; and

FIG. 3 depicts the showing of FIG. 2 partially cutaway with the bolus of the invention enclosed in a resilient housing.

DETAILED DESCRIPTION OF THE INVENTION

Figure 1:
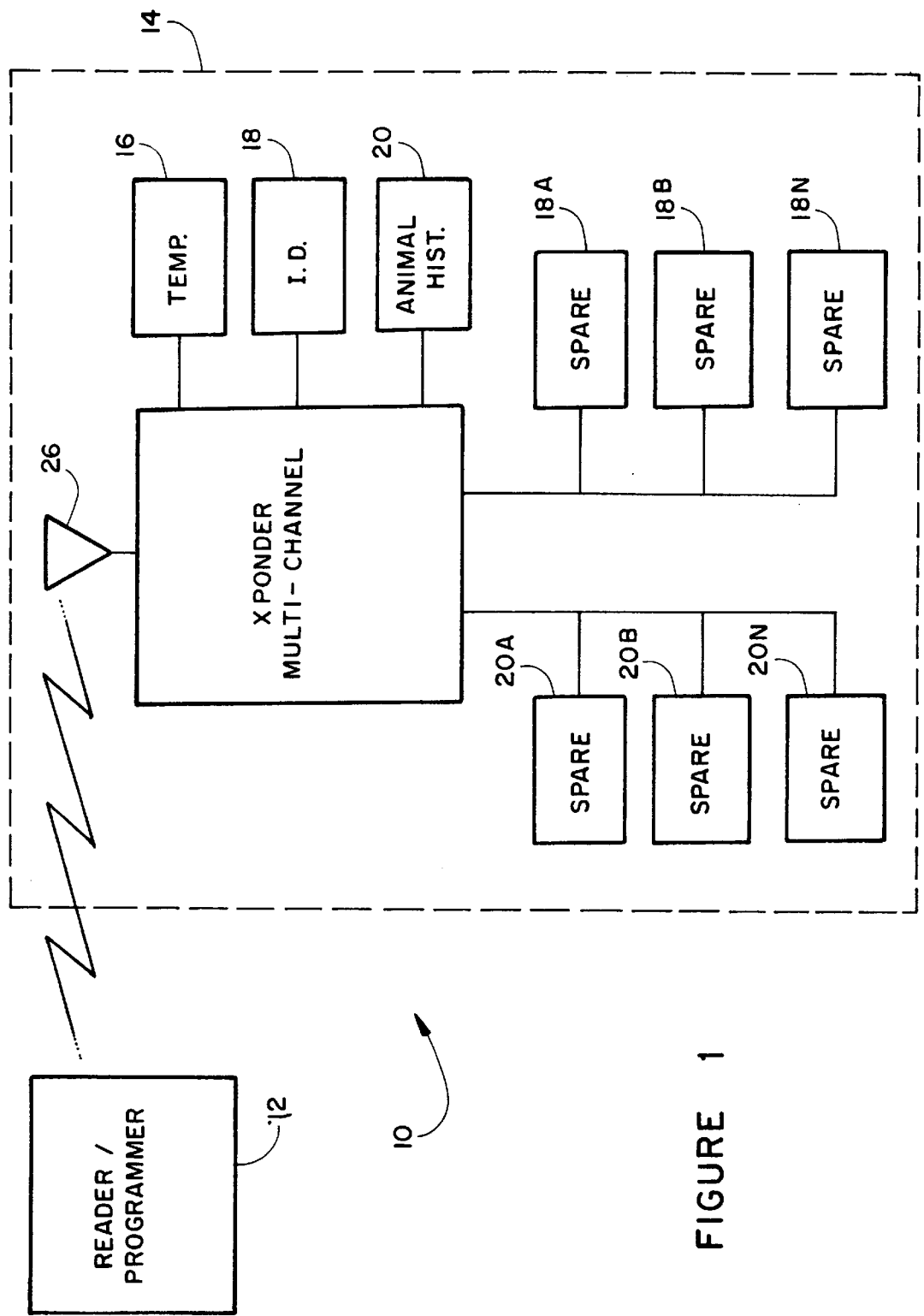
FIG. 1 depicts a block diagram of the invention.

The device 10 comprises a read/write scanner 12 of the type DAS-5004 manufactured by BioMedic Data Systems, Inc. of Seaford, Del. or an equivalent thereto suitable for the purpose intended, namely, to read or write into memories carried by a transponder. The read/write scanner 12 transmits a signal to a transponder 14 located remotely from the read/write scanner as for example a transponder placed in a ruminant animal. The transponder 14 may be of the type IPTT, also manufactured by BioMedic or an equivalent thereto suitable for the purpose intended.

Attached to the transponder for reading by the read/write scanner 12 are a plurality of both read only (16–16N, 18–18N) and programmable/read memories (20–20N).

Memories contained on the transponder chip providing useful data may be monitored by the read/write scanner 14 using read only preprogramed memories, as for example, animal identification 18 and other data on memories 18A–18N to be monitored only and unprogrammable during the life of the animal. Programmable/readable memories 20–20N, such as, one containing a running log of animal medical history which can be updated periodically with current medical information or any other important information during the life of the animal. With this medical or other important information being burnt in and non-erasable externally of the animal.

It should be understood that redundant information can be stored in like chips 18 and 20 or the additional chips 18A–18N and 20A–20N can be used as spares for later determined vital information on the animal.

The transponder chip is attached by any suitable means, such as, by way of example, an adhesive such as epoxy or the like to the outer surface of a coated ferrite magnet 22 such as a rectilinear block magnet or the like obtainable from POWER MAGNETS, USA. The magnetic should have sufficient weight to remain in the animal throughout its life and be reusable. Typical weight of a magnetic bolus being in the range of 2 to 6 ounces.

A wire antenna 26 of a suitable conductor is connected to the input/output of the transponder 14 by wrapping several turns around the magnet over the transponder and chips all being fixedly in place on the magnet. The antenna is likewise affixed to the magnet by suitable means as noted above. Preferably, the field of the magnetic will be normal to the field developed in the winding 26. Thus, the permanent magnet can be used as the magnetically permeable core of the antenna winding 26 acting as an inductor. It has been found that random wrapping of the antenna about the magnet successfully operates by under certain conditions may require incased power transmission from the reader/programmer. It has been also found that as the animal in which the bolus is placed ingests metal objects through its life that the operation of the device improves due to the magnet attached metal objects increasing the antenna efficiency.

The entire device can then be inserted into a length of shrink tubing 28 or the like with the ends sealed and the tubing shrunk around the complete bolus and electronics. The shrink tubing or the like should be of sufficient thickness to with stand an animal bite when being initially placed in the animal without causing damage to the windings, transponder(s) or micro chips.

It should be understood that the transponder chip and the specific memories implanted therein are state of the art small micro-circuitry.

It should be understood that the above description is only illustrative of the principles of the present invention, and that one of ordinary skill in the art could readily devise numerous modifications and additions to the invention as discussed above without departing from e spirit and slope.

I claim:

1. A bolus for oral administration to a ruminant animal and for retention in the rumen or reticulum of that animal comprising:

a permanent magnet;

a transponder chip;

at least one read only memory containing identification information of said animal carried by said transponder chip;

an antenna connected to said transponder chip for transmitting at least said identification contained on said at least one memory when said transponder chip is excited, said antenna comprising a plurality of wire windings around said magnet; and a reader for exciting said transponder chip and reading at least said identification on said at least one memory;

said transponder chip, at least one read only memory and antenna all being fixedly attached to said magnet.

2. The invention as defined in claim 1 wherein said magnet is a ferrite permanent magnet.

3. The invention as defined in claim 1 wherein said magnet is rectilinearly configured.

4. The invention as defined in claim 1 wherein said transponder chip can receive information from said reader and can transmit information to said reader.

5. The invention as defined in claim 1 additional comprising a plurality of additional read only memories.

6. The invention as defined in claim 1 additionally comprising at least a second read only memory carried by said transponder chip for providing a second specific different information related to said ruminant.

7. The invention as defined in claim 1 wherein said reader is additionally a programmer and in addition to said at least one read only memory at least one read/programmable memory is carried by said transponder chip in a manner that through said transponder chip said at least one read/programmable memory can be programed and read by said reader.

8. The invention as defined in claim 7 additionally including a plurality of read/programmable memories.

9. The invention as defined in claim 1 wherein said plurality of wire wrappings of said antenna are wound normal to the flux of said permanent magnet.

10. The invention as defined in claim 1 wherein said plurality of wire wrappings of said antenna are randomly wound around said permanent magnet.

* * * * *